United States Patent
Abney et al.

(10) Patent No.: US 10,308,462 B2
(45) Date of Patent: Jun. 4, 2019

(54) PLATE FOR AN ANVIL ROLL WITH A REDUCED-VACUUM REGION FOR USE IN A SLIP AND CUT SYSTEM AND METHOD OF USING THE SAME

(71) Applicant: Kimberly-Clark Worldwide, Inc., Neenah, WI (US)

(72) Inventors: Patrick Dean Abney, Menasha, WI (US); Paul Douglas Beuther, Neenah, WI (US); Kevin Gerald Dolan, Neenah, WI (US); David John Enz, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 591 days.

(21) Appl. No.: 14/020,256

(22) Filed: Sep. 6, 2013

(65) Prior Publication Data

US 2015/0068372 A1 Mar. 12, 2015

(51) Int. Cl.
*B65H 20/12* (2006.01)
*B26F 1/20* (2006.01)
(Continued)

(52) U.S. Cl.
CPC ....... *B65H 20/12* (2013.01); *A61F 13/15764* (2013.01); *B26D 7/018* (2013.01);
(Continued)

(58) Field of Classification Search
CPC ............. Y10T 83/0443; Y10T 83/0453; Y10T 83/0467; Y10T 83/207; Y10T 83/2185;
(Continued)

(56) References Cited

U.S. PATENT DOCUMENTS

| 4,437,659 | A | 3/1984 | Caron et al. |
| 4,724,036 | A | 2/1988 | Hill et al. |

(Continued)

FOREIGN PATENT DOCUMENTS

| EP | 2581068 A2 | 4/2013 |
| WO | 2013089009 A1 | 6/2013 |

OTHER PUBLICATIONS

Notification of Transmittal of the International Search Report and the Written Opinion of the International Searching Authority for International Application No. PCT/IB2014/063939, dated Mar. 13, 2015; 11 pages.

(Continued)

*Primary Examiner* — Phong H Nguyen
(74) *Attorney, Agent, or Firm* — Armstrong Teasdale LLP (57) ABSTRACT

A plate configured to contact a web includes a first region having a first characteristic and a second region having a second characteristic different than the first characteristic. The plate has a substantially arcuate wall with an inner surface and an outer surface. A plurality of vacuum holes extends between the inner and outer surfaces and are configured to be in fluid communication with a vacuum source. A vacuum region is adapted to contact the first region of the web and a reduced-vacuum region is adapted to receive the second region of the web. The plurality of vacuum holes are configured such that, when attached to the vacuum source, a vacuum pressure at the vacuum region is greater than a pressure at the reduced-vacuum region so that the first region of the web is held against the plate with a greater force than the second region.

16 Claims, 10 Drawing Sheets

(51) Int. Cl.
  *B26D 7/01* (2006.01)
  *B65H 27/00* (2006.01)
  *A61F 13/15* (2006.01)

(52) U.S. Cl.
  CPC .............. *B26F 1/20* (2013.01); *B65H 27/00* (2013.01); *B65H 2301/5151* (2013.01); *B65H 2406/331* (2013.01); *B65H 2801/57* (2013.01); *Y10T 83/04* (2015.04); *Y10T 83/6648* (2015.04)

(58) Field of Classification Search
  CPC .. Y10T 83/2196; Y10T 83/6648; A61F 13/15; B65H 20/12; B65H 20/10; B65H 27/00; B65H 2301/5151; B65H 2406/331; B65H 2406/33; B65H 2406/332; B65H 2801/57; B26D 7/018; B26F 1/20
  USPC .................................. 269/20, 21; 248/309.3
  See application file for complete search history.

(56) References Cited

U.S. PATENT DOCUMENTS

| | | | |
|---|---|---|---|
| 5,135,614 A | | 8/1992 | Aula et al. |
| 5,183,252 A | | 2/1993 | Wolber et al. |
| 5,407,507 A | | 4/1995 | Ball |
| 5,486,253 A | | 1/1996 | Otruba |
| 5,681,075 A | * | 10/1997 | Komori .................. B60H 1/28 296/192 |
| 5,706,994 A | | 1/1998 | Welch et al. |
| 6,149,755 A | | 11/2000 | McNichols et al. |
| 6,350,223 B1 | | 2/2002 | Niedermeyer |
| 6,494,244 B2 | | 12/2002 | Parrish et al. |
| 6,915,829 B2 | | 7/2005 | Popp et al. |
| 7,037,404 B2 | | 5/2006 | Cavalotti et al. |
| 7,533,709 B2 | | 5/2009 | Meyer |
| 7,537,215 B2 | | 5/2009 | Beaudoin et al. |
| 7,618,513 B2 | | 11/2009 | Meyer |
| 8,069,894 B2 | * | 12/2011 | Yamamoto ........ A61F 13/15723 156/519 |
| 2002/0050324 A1 | | 5/2002 | Middlestadt et al. |
| 2004/0007328 A1 | | 1/2004 | Popp et al. |
| 2004/0089516 A1 | * | 5/2004 | Christian .......... A61F 13/15723 198/459.8 |
| 2005/0230056 A1 | | 10/2005 | Meyer et al. |
| 2006/0266466 A1 | * | 11/2006 | Meyer ............... A61F 13/15699 156/250 |
| 2007/0084580 A1 | | 4/2007 | Kahl et al. |
| 2009/0294044 A1 | | 12/2009 | Gill et al. |
| 2012/0073417 A1 | * | 3/2012 | Ujiie ...................... B26D 7/018 83/24 |
| 2012/0247661 A1 | | 10/2012 | Ogasawara et al. |

OTHER PUBLICATIONS

Extended European Search Report for Application No. 14842945.9, dated Nov. 28, 2017, 9 pages.

* cited by examiner

PLATE FOR AN ANVIL ROLL WITH A REDUCED-VACUUM REGION FOR USE IN A SLIP AND CUT SYSTEM AND METHOD OF USING THE SAME

BACKGROUND

The present disclosure relates generally to a vacuum slip roll used in the manufacture of an article. More particularly, some aspects of the disclosure relate to an anvil roll, anvil-roll plate, and/or a slip-and-cut system used in the manufacture of an absorbent article or the like and the methods of using the same.

Many absorbent articles intended for personal wear, such as diapers, training pants, feminine hygiene products, adult incontinence products, bandages, medical garments, and the like have been manufactured by processes wherein discrete parts or segments of the article are deposited on a continuously moving product web. In such processes, a vacuum slip roll, anvil roll, or the like may be used when cutting, transporting, and transferring the segment to the moving product web. For example, a known slip-and-cut manufacturing process uses a vacuum drum rotating at a speed faster than an incoming web from which the segment is to be cut. The incoming web thus slips on the drum surface until a cut-off knife cuts a correct length of the web thereby forming the segment. The cut-off knife may be mounted on a cutting roll which moves with a surface velocity similar to that of the rotating vacuum drum and which cuts the segment from the incoming web when the knife comes into contact with the rotating vacuum drum. The cut segment is held to the surface of the drum by a vacuum drawn through holes provided in the drum. The segment is held and transported on the drum to a transfer point where the segment is transferred to the continuously moving product web forming at least a portion of the absorbent article.

However, one or more problems may arise when using this known process for non-uniform incoming webs. That is, in some applications, the incoming web (i.e., the web from which the discrete segments are to be cut) may comprise multiple regions of material comprising differing mechanical properties. For example, the incoming web may comprise a base substrate with one or more fastening components disposed thereon. The one or more fastening components may comprise any suitable material used to fasten the absorbent article about a wearer, such as a hook material. In such cases, this non-uniformity of the incoming web may cause problems when the incoming web slips on the surface of the vacuum drum. For example, the fastening (e.g., hook) material may engage the slip surface with a greater friction force than the surrounding base substrate of the incoming web thereby causing undesired wear in the region of the vacuum drum contacted by the fastening region. Further, when the fastening component comprises a hook material, the hooks may become warn or deformed due to the hooks interaction with the rotating drum surface.

Thus, there remains a need for a vacuum drum that eliminates one or more of the problems caused by known slip-and-cut processes when manufacturing absorbent articles or the like. More specifically, there remains a need for an improved vacuum slip drum to be used when cutting and transporting discrete segments from non-uniform incoming webs.

BRIEF DESCRIPTION

In one aspect, a plate is configured to contact a web including a first region having a first characteristic and a second region having a second characteristic different than the first characteristic. The plate generally comprises a substantially arcuate wall comprising an inner surface, an outer surface, and a plurality of vacuum holes extending between the inner and outer surfaces and configured to be in fluid communication with a vacuum source. At least one vacuum region is adapted to contact the first region of the web and at least one reduced-vacuum region is adapted to receive the second region of the web. The plurality of vacuum holes are configured such that, when attached to the vacuum source, a vacuum pressure at the at least one vacuum region is greater than a pressure at the at least one reduced-vacuum region so that the first region of the web is held against the plate with a greater force than the second region.

In another aspect, a slip-and-cut system generally comprises a web feeding assembly, a knife roll, and an anvil roll. The anvil roll comprises a drum having an inner surface and an outer surface; a plurality of vacuum holes extending between the inner surface and the outer surface; and at least one vacuum region and at least one reduced-vacuum region on the outer surface. The web feeding assembly is configured to feed a web having a base substrate and a fastening material to the anvil roll at a speed slower than a surface speed of the anvil roll such that the web slips along the outer surface of the anvil roll. The knife roll is configured to contact the web slipping on the outer surface of anvil roll and cut a segment free from the web. The anvil roll is configured to transport the segment via a vacuum pressure applied to the outer surface of the vacuum roll by a vacuum source. The plurality of vacuum holes are configured such that a vacuum pressure at the at least one vacuum region is greater than a vacuum pressure at the at least one reduced-vacuum region wherein. When the web slips along the outer surface of the anvil roll, the base substrate abuts the at least one vacuum region and the fastening material abuts the at least one reduced-vacuum region such that the base substrate of the web is held against the anvil roll with a greater force than the fastening material.

In yet another aspect, a method of making a web segment from a continuous web. The method generally comprises feeding a web comprising a base substrate and a fastening material to an anvil roll of a slip-and-cut system. The anvil roll has a vacuum region and a reduced-vacuum region. The base substrate of the web is generally aligned with the vacuum region and the fastening material is generally aligned with the reduced-vacuum region. The anvil roll is driven such that the surface speed of the anvil roll is greater than a speed at which the continuous web is fed to the anvil roll such that the web slips relative to the anvil roll. A discrete segment is cut from the continuous web while the web is slipping relative to the anvil roll.

DETAILED DESCRIPTION OF THE DRAWINGS

Figure 1:
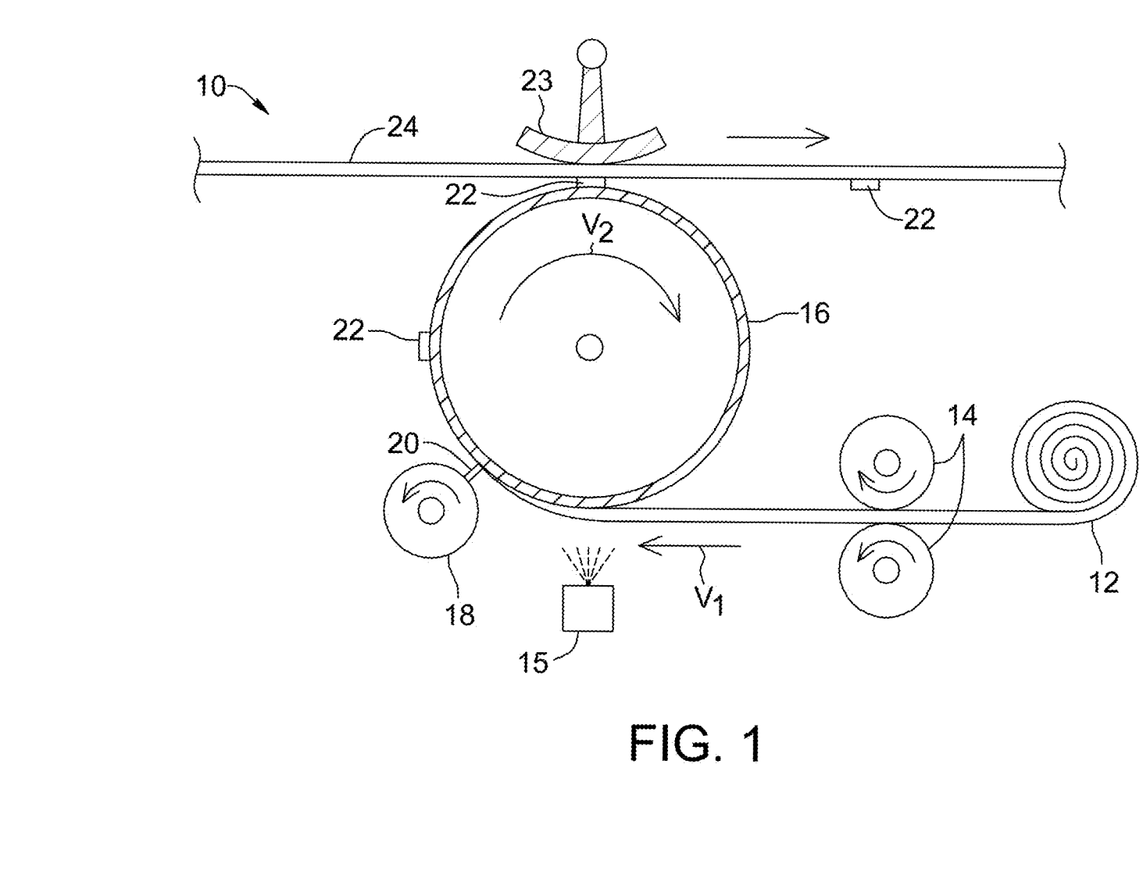
FIG. 1 is a side view of a slip-and-cut system according to one embodiment of the disclosure.

Turning now to the drawings, FIG. 1 illustrates a suitable slip-and-cut system, indicated generally at 10, according to one embodiment of the disclosure used to form absorbent articles. The absorbent articles may be, e.g., diapers, training pants, feminine hygiene products, adult incontinence products, bandages, medical garments, and the like. The slip-and-cut system 10 may be used to deposit a discrete part or segment 22 on a continuously moving product web 24. Specifically, an incoming web 12 may be fed to an anvil roll 16 via a web feeding assembly such as, e.g., one or more drive rollers 14. In the illustrated embodiment, a suitable adhesive is applied to the web 12 at an adhesive station 15 prior to or upon reaching the anvil roll 16. It is understood that the adhesive station 15 could be positioned at different location in the system 10. It is also understood that in other suitable embodiments the adhesive station 15 can be omitted.

Figure 3:
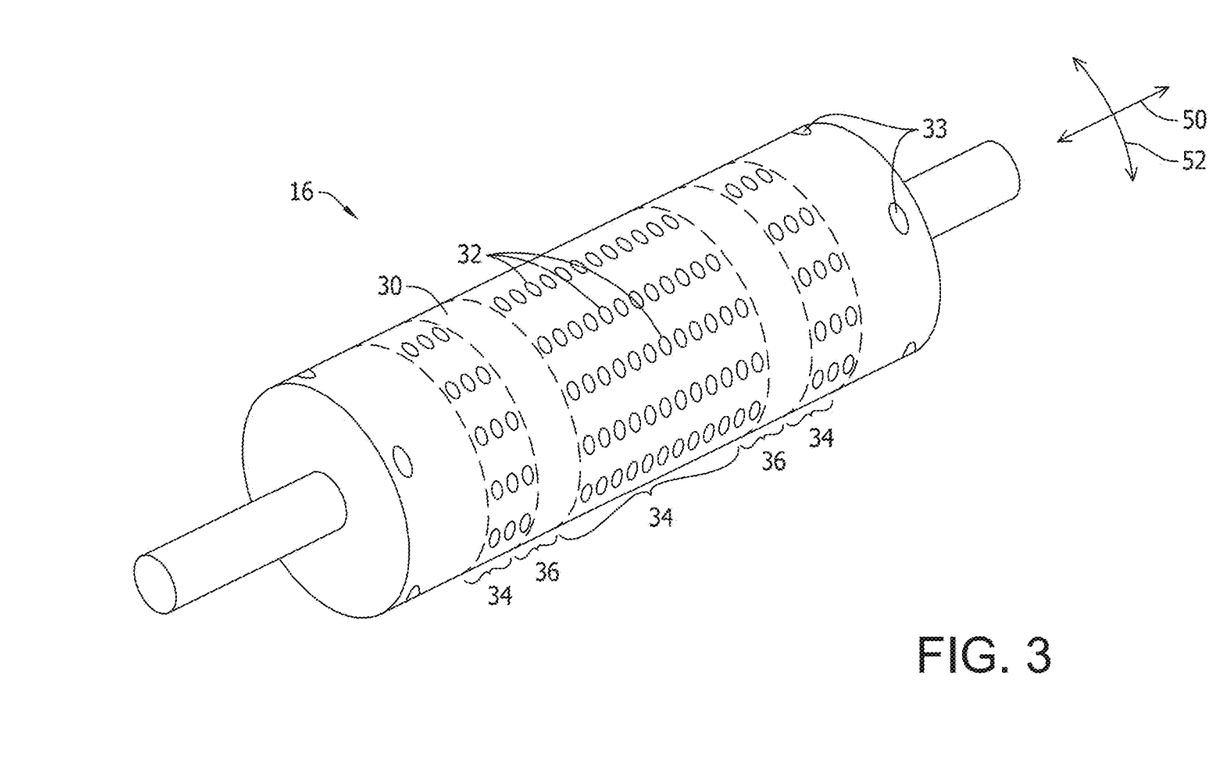
FIG. 3 is a perspective of one embodiment of an anvil roll used in the slip-and-cut system of FIG. 1.

In the illustrated embodiment, the anvil roll 16 is a vacuum roll formed as a cylindrical drum having an inner surface 29, an outer surface 30, and one or more vacuum holes 32 extending between the inner surface and the outer surface (FIG. 3). The anvil roll 16 may internally contain or otherwise be connected to a suitable vacuum source (such as, e.g., a vacuum pump, a vacuum chamber, etc., not shown) which is capable of selectively applying vacuum pressure (i.e., negative pressure) through the one or more vacuum holes 32 such that materials located on the outer surface 30 of the anvil roll are generally drawn to and secured against the outer surface. In some embodiments, the vacuum source may be capable of applying a vacuum in the range of 1 to 20 inches of water, and more preferably in the range of 3 to 10 inches of water, and even more preferably in the range of 4 to 7 inches of water.

In one suitable embodiment, the incoming web 12 is fed to the anvil roll 16 at a slower linear speed (as indicated by $V_1$ in FIG. 1) than the surface speed of the anvil roll (as indicated by $V_2$ in FIG. 1). In other words, the surface speed of the anvil roll 16 is greater than the speed at which incoming web 12 is fed to the anvil roll. As a result, the leading edge of incoming web 12 engages and slips against the outer surface 30 of the anvil roll 16. It is understood that the incoming web 12 can be fed to the anvil roll 16 at any suitable rate. For example, in one suitable embodiment, the incoming web 12 is fed to the anvil roll 16 at a rate between about ½ and about 1/20 the surface speed of the anvil roll. In other words, the surface speed of the anvil roll 16 is between about twice and about twenty times greater than the speed at which the incoming web 12 is fed to the anvil roll. In one preferred embodiment, the incoming web 12 is fed to the anvil roll 16 at a rate about 1/10 the surface speed of the anvil roll. In other words, the surface speed of the anvil roll is ten times greater than the speed at which the incoming web is fed to the anvil roll.]

The slip-and-cut system 10 illustrated in FIG. 1 further comprises a knife roll 18 having one or more knife edges 20 (one knife edge being illustrated in FIG. 1). As seen in FIG. 1, the knife edge 20 is oriented in a longitudinal direction 50 on the knife roll 18 (i.e., a direction substantially parallel to a center axis of the knife roll and the anvil roll 16) and may be configured to cut material provided on the outer surface 30 of the anvil roll when the knife edge comes in contact with the surface of the anvil roll. Thus, when the incoming web 12 is fed to the anvil roll 16, the knife edge 20 will cut the incoming web in a cross-machine or transverse direction when the knife edge comes into contact with the surface 30 of the anvil roll thereby forming a discrete segment 22.

For example, in the illustrated embodiment, the knife roll 18 comprises one knife edge 20 such that the slip-and-cut system 10 is configured to cut the incoming web 12 once per rotation of the knife roll. That is, for each complete rotation of the knife roll 18, the knife edge will come into contact with the outer surface 30 of the anvil roll 16 one time, thus forming one segment 22 per rotation of the knife roll. In other embodiments, the knife roll 18 may comprise more than one knife edge 20 such that the slip-and-cut system 10 is configured to cut the incoming web 12 more than one time per rotation of the knife roll 18 as will be appreciated by those skilled in the art.

Once the segment 22 has been cut from the incoming web 12 by the knife roll 18, the segment will be transported at the surface speed of the anvil roll 16 to the continuously moving product web 24. That is, once cut from the incoming web 12, the segment 22 will be held to the outer surface 30 of anvil roll 16 via the vacuum drawn through the vacuum holes 32 extending between the inner and outer surfaces of the anvil roll. The segment 22 will thus travel at the same surface speed as the anvil roll 16 until it reaches the product web 24, where it is deposited on the product web to form a portion of the absorbent article.

In the illustrated embodiment, each of the segments 22 are adhered to the moving product web 24. More specifically, the segment 22 having adhesive thereon and the moving product web 24 are directed through a nip defined by the anvil roll 16 and a stomper 23 (or other suitable device, e.g., a roll). It is understood that the segment 22 can bonded to the moving product web using any suitable bonding technique.

The combined product web 24 and segment 22 are then moved downstream for further processing (e.g., cutting into discrete absorbent articles, folding of the absorbent articles, packaging of the absorbent articles, etc.). In one suitable embodiment, the moving product web 24 is being fed at the rate substantially equal to the rate (i.e., the speed of the outer surface 30 of the anvil roll 16) at which the segment 22 is being delivered thereto.

Figure 2:
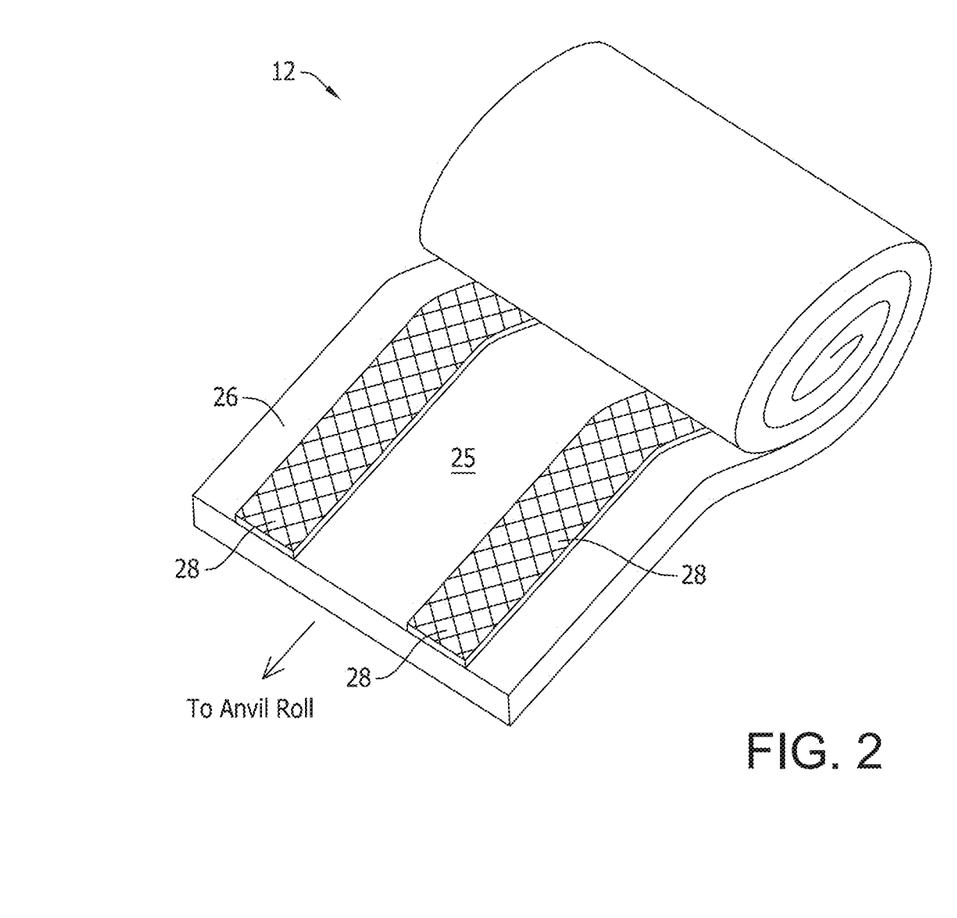
FIG. 2 is a perspective of an example web used in the slip-and-cut system of FIG. 1.

Turning now to FIG. 2, in one suitable embodiment, an anvil-facing surface 25 of the incoming web 12 (i.e., a surface intended to abut the outer surface 30 of the anvil roll 16) may be non-uniform (i.e., may contain regions having different heights, constructed of different materials, comprising different mechanical or physical properties (e.g., strength, porosity, density), etc.). Thus, the non-uniform web has regions comprising different characteristics. That is, the incoming web 12 has at least two regions with one of the regions (a first region) having a first characteristic and a second region having a second characteristic different than the first characteristic.

In the illustrated embodiment, the anvil-facing surface 25 of the incoming web 12 illustrated in FIG. 2 comprises a base substrate 26 with one or more strips of fastening material 28 (e.g., a suitable male fastening material) extruded on or otherwise attached to the base substrate. In the depicted embodiment, for example, the incoming web 12 comprises two strips of fastening material 28 extruded onto the base substrate 26, but, in other embodiments, the incoming web 12 may have any number of strips of fastening materials 28 and/or other non-uniform components along the anvil-facing surface 25.

Figure 8:
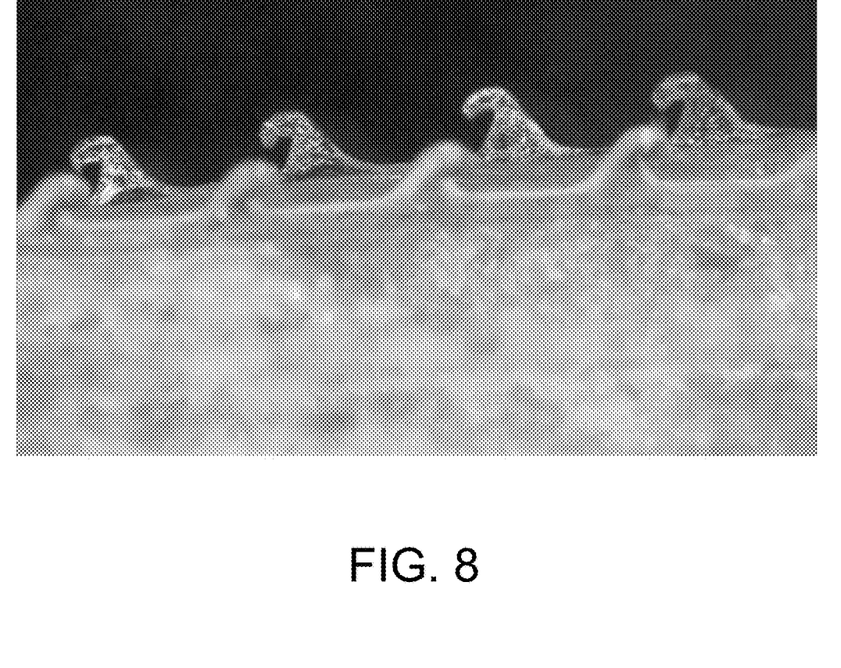
FIG. 8 is a photograph of undamaged hooks of a fastening material.
Figure 9:
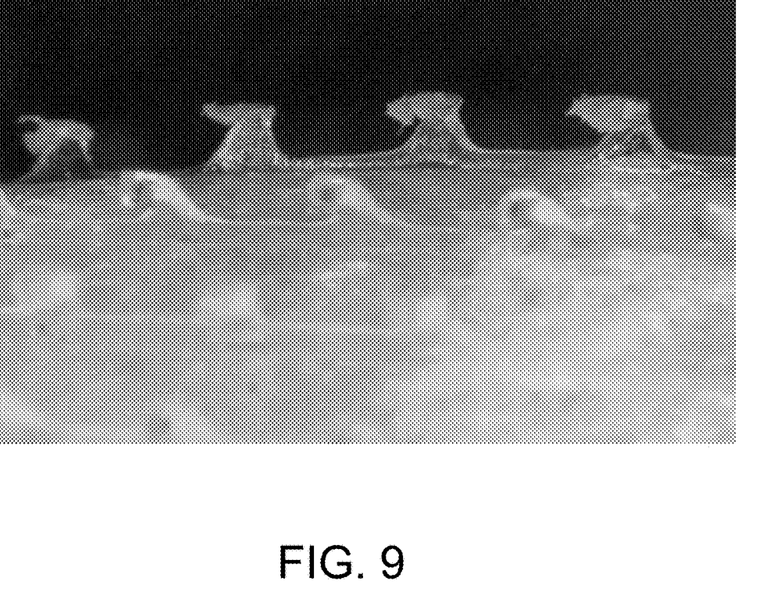
FIG. 9 is a photograph of damaged hooks of a fastening material.

As illustrated in FIG. 3, the anvil roll 16 is configured to accommodate the non-uniform, anvil-facing surface 25 of the incoming web 12. That is, if a vacuum pressure is approximately equal along the longitudinal direction 50 of the anvil roll, the non-uniform anvil-facing surface 25 of the incoming web 12 may cause one or more problems. For example, in some embodiments, the fastening material 28 is, e.g., a male fastening material, and more preferably, a polymer (e.g., polyethylene, polypropylene) hook material. In such embodiments, when the anvil-facing surface 25 of the incoming web 12 slips against the anvil roll 16, the hooks may cause undesirable wear in the surface 30 of the anvil roll. That is, the vacuum may draw the incoming web 12 into the surface 30 of the anvil roll 16, causing excessive friction in the circumferential areas of the surface contacted by the hooks of the fastening material 28. Further, and particularly when the fastening material 28 (e.g., hooks) is made from a relatively soft material such as polyethylene, the interaction of the hooks with the surface 30 of the anvil roll 16 may cause the hooks to deform or otherwise wear. For example, the slipping of the hooks against the surface 30 of the anvil roll 16 may cause a top of the hooks to compress and flatten, while interaction of the hooks with the vacuum holes 32 may cause the hooks to bend, deform, or even shear. FIG. 8, for example, is a photograph taken of undamaged hooks and FIG. 9 is a photograph taken of hooks damaged by a slip and cup system and more specifically by contact with an anvil roll.

Accordingly, in some embodiments of the disclosure, a vacuum pressure at an area of the anvil roll 16 which interacts with the fastening material 28 is reduced or eliminated, thus reducing the friction force on the fastening material when the incoming web 12 slips on the anvil roll and/or when the segment 22 is transported by the anvil roll. This may be more readily understood with reference to FIG. 3. FIG. 3 illustrates a first embodiment of the anvil roll 16 of the slip-and-cut system 10 used to reduce the vacuum in an area of the anvil roll which ultimately abuts the fastening material 28 during use. As seen in FIG. 3, the anvil roll 16 comprises a plurality of vacuum holes 32. The anvil roll 16 may further comprise other apertures or the like, such as a plurality of mounting holes 33, without departing from the scope of this disclosure.

As seen, the plurality of vacuum holes 32 are arranged on the surface 30 of the anvil roll 16 such that the surface comprises vacuum regions 34 and reduced-vacuum regions 36. More particularly, the vacuum regions 34 are portions of the surface 30 where the vacuum holes 32 are provided regularly about the circumference of the anvil roll 16. These vacuum regions 34 tend to draw material against the outer surface 30 of the anvil roll 16 (such as incoming web 12) when the material is provided to the anvil roll. In contrast, the reduced-vacuum regions 36 in the illustrated embodiment are defined by portions of the outer surface 30 where vacuum holes 32 are not provided regularly about the circumference of the anvil roll 16 (e.g., bands around the circumference of the surface containing no holes). According, a material provided to the outer surface 30 of the anvil roll 16 will tend not to be drawn against the anvil roll at the reduced-vacuum regions 36 or drawn against the anvil roll to a lesser extent compared to the material aligned with the vacuum regions 34.

The vacuum regions 34 of the anvil roll 16 may be provided at an appropriate position in the longitudinal direction 50 such that the vacuum regions generally align with the base substrate 26 of the anvil-contacting surface 25 of the incoming web 12, while the reduced-vacuum regions 36 may be provided at an appropriate position in the longitudinal direction such that the reduced-vacuum regions generally align with the fastening material 28 of the anvil-contacting surface of the incoming web. In the illustrated embodiment, the base substrate 26 comprises a nonwoven web having a relatively high porosity. The fastening material 28 on the other hand has a relatively low porosity. In one suitable embodiment, the fastening material 28 is fluid impermeable whereas the base substrate 26 is fluid permeable.

In such embodiments, a vacuum (negative) pressure provided by a vacuum source will be higher at portions of the surface 30 of the anvil roll 16 contacting the base substrate 26, and lower or even eliminated at portions of the surface of the anvil roll contacting the fastening material 28. Because the friction force between the fastening material 28 and the outer surface 30 of the anvil roll 16 is reduced along the bands abutting the fastening material (due to the reduced vacuum pressure provided in the reduced-vacuum regions 36) the surface of the anvil roll may not be as prone to wear or as much wear in those regions. Further, and particularly when the fastening material 28 comprises a hook material made from, e.g., polymer, the reduced friction force provided in the reduced-vacuum region 36 may reduce or eliminate damage to the hooks caused by known slip-and-cut systems. For example, the reduced friction force in the reduced-vacuum regions 36 may reduce or eliminate the compression of the polymer hooks, such that the hooks are not deformed when ultimately transferred to the product web 24. Still further, and because there is a reduced vacuum in the reduced-vacuum regions 36 of the illustrated anvil roll 16, the hooks will not engage with the vacuum holes when slipping on the surface 30 of the anvil roll. Accordingly, this reduces or eliminates the shearing, bending, or otherwise deforming of the hook fasteners that otherwise may occur due to the engagement of the hooks with the vacuum holes.

Although the anvil roll 16 depicted in FIG. 3 is shown with no vacuum holes 32 in the reduced-vacuum regions 36, in other embodiments, the reduced-vacuum regions may comprise vacuum holes 32 yet still provide a reduced vacuum pressure without departing from the scope of this disclosure. For example, in some embodiments, the vacuum holes 32 may be provided in the reduced-vacuum region 36 albeit less densely than those provided in the vacuum region 34. That is, the anvil roll 16 may comprise less vacuum holes per unit area in the reduced-vacuum region 36 than in the vacuum region 34 such that a vacuum pressure (and corresponding friction force, etc.) will be less in the reduced-vacuum region than in the vacuum region.

Further, for known anvil rolls comprising evenly distributed vacuum holes 32 along its surface, some or all of the holes within the reduced-vacuum region may be plugged to reduce the vacuum pressure and/or friction force within the reduced-vacuum region 36 such as by, e.g., placing tape over some of the vacuum holes, inserting set screws into some of the vacuum holes, etc.

Alternatively, the vacuum holes 32 may be provided in the reduced-vacuum region 36 with smaller diameters than those provided in the vacuum region 34 thus providing a reduced vacuum pressure in the reduced-vacuum region. Still further, in other embodiments, the shape of the vacuum holes 32 provided in the reduced-vacuum region 36 may be altered such that the vacuum pressure and/or friction force in the reduced-vacuum region is reduced as compared to known slip-and-cut systems. For example, in some embodiments, a cross-sectional profile of the vacuum holes 32 in the reduced-vacuum region 36 may be altered to reduce the vacuum pressure and/or friction force in the reduced-vacuum region, as will be discussed more fully in connection with FIGS. 5A-5D.

Figure 4:
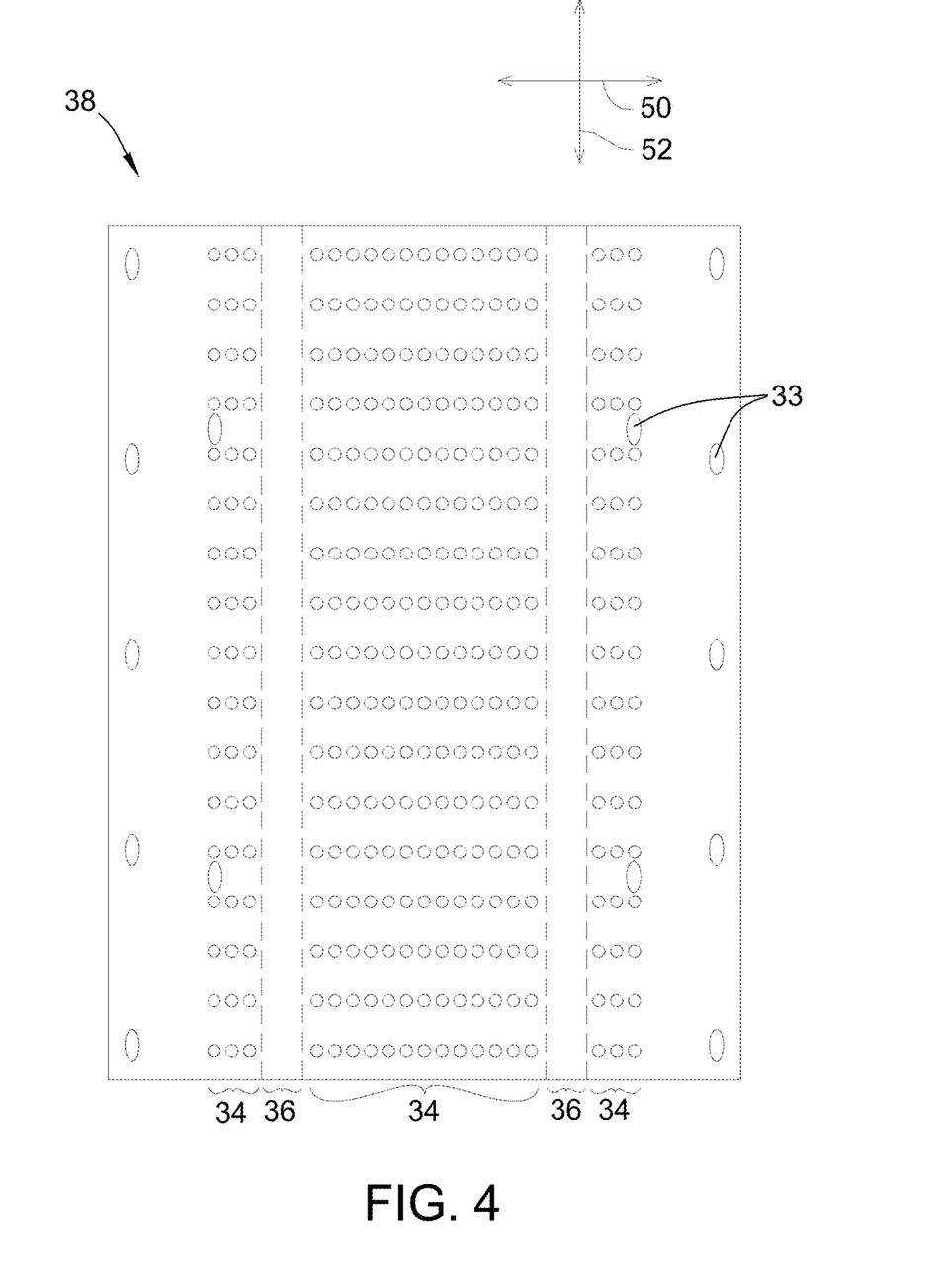
FIG. 4 is a laid-flat view of an anvil-roll plate as part of the anvil roll of FIG. 3.

Turning now to FIG. 4, in some embodiments, the anvil roll 16 comprising the reduced-vacuum regions 36 may be formed using one or more arcuate plates attached to a vacuum drum or the like. FIG. 4 is a laid-flat view of one arcuate anvil-roll plate 38 according to some embodiments of the disclosure. The anvil-roll plate 38 may be formed using any suitable material, and in some cases may be constructed of, e.g., metal (such as stainless steel), plastic, carbon fiber. Although shown as a plan view in FIG. 4 (i.e., a substantially flat configuration), it will be appreciated that in practice the anvil-roll plate 38 will have an arcuate cross-section with a radius of curvature approximately equal to the radius of the anvil roll 16.

The anvil-roll plate 38 has an inner surface (not shown in FIG. 4) and outer surface 30, with the vacuum holes 32 extending between the inner and outer surfaces and configured such that the vacuum regions 34 and non-vacuum regions 36 are formed in the anvil-roll plate. As discussed in connection with FIG. 3, the vacuum regions 34 are regions of the anvil-roll plate 38 where vacuum holes 32 are provided regularly about the circumference of the anvil-roll plate, while the reduced-vacuum regions are regions of the anvil-roll plate where vacuum holes are not provided regularly about the circumference of the anvil-roll plate. Alternatively, the reduced-vacuum regions 36 may be regions of the anvil-roll plate 38 where the vacuum holes 32 are provided less densely than in the vacuum regions 34, where the vacuum holes are smaller than those in the vacuum regions, where a cross-sectional profile of the vacuum holes differ from those in the vacuum region, etc.

In some embodiments, it may be desirable to have a greater vacuum force at certain areas of the vacuum regions 34 of the anvil roll 16 than at other areas. Thus, in some areas of the vacuum regions 34 a density of the vacuum holes 32 may be greater in one area such that a vacuum pressure at that area is correspondingly greater. In such embodiments, when ultimately provided on a vacuum drum or the like, a greater vacuum pressure and/or friction force may act on the incoming web 12 at certain circumferential areas than at others areas. Nonetheless, even in such embodiments, the reduced-vacuum regions 36 are configured to provide a reduced vacuum pressure and/or friction force as compared to the vacuum regions 34 within the more dense areas.

By providing an anvil-roll plate 38 with a pattern of vacuum holes 32 configured to provide a reduced vacuum pressure and/or reduced friction force in certain regions of the plate (e.g., in reduced-vacuum regions 36), known slip-and-cut systems may be retrofitted in order to effectively process, e.g., an incoming web 12 with a non-uniform anvil-facing surface 25. For example, vacuum or anvil rolls within the slip-and-cut system may be configured such that plates containing vacuum holes may be removed or replaced according to a specific application, for maintenance of the drum and/or plate, etc. Accordingly, when using a slip-and-cut system to, e.g., manufacture absorbent articles comprising segments 22 (made from the non-uniform incoming web 12), the anvil drum may be fitted with the anvil-roll plate 38. In such embodiments, a reduced vacuum pressure and/or friction force may be provided at a location where the anvil roll 16 abuts the fastening material 28 of the incoming web 12.

Figure 5A:
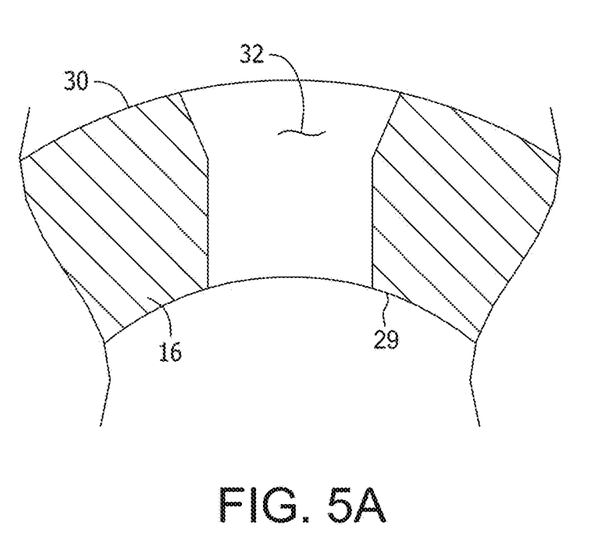
FIGS. 5A-5D are cross-sectional views of alternative embodiments of vacuum holes provided in the surface of the anvil roll of FIG. 3.

In other embodiments, the shape and/or mechanical properties of the anvil roll 16 and/or the vacuum holes provided therein may be altered in order to reduce a vacuum pressure and/or friction force in an area of the anvil roll which abuts the fastening material 28 of the incoming web 12. This may be more readily understood with reference to FIGS. 5-7. First, FIGS. 5A-5D depict a cross-sectional profile view of vacuum holes 32, 46, 146, 246, respectively, provided in the anvil roll 16 according to some aspects of the disclosure. As discussed, the vacuum holes 32, 46, 146, 246 may extend between the inner and outer surfaces of the anvil roll 16 such that a vacuum source draws material (e.g., incoming web 12) to the surface of the anvil roll. As seen in FIG. 5A, in some embodiments, the vacuum hole 32 may comprise a generally uniform cross-section. For example, the vacuum hole 32 may be a hole with a uniform diameter along its entire axial length. That is, the diameter of the hole 32 adjacent the inner surface is substantially equal to the diameter of the hole adjacent the outer surface.

Figure 5B:
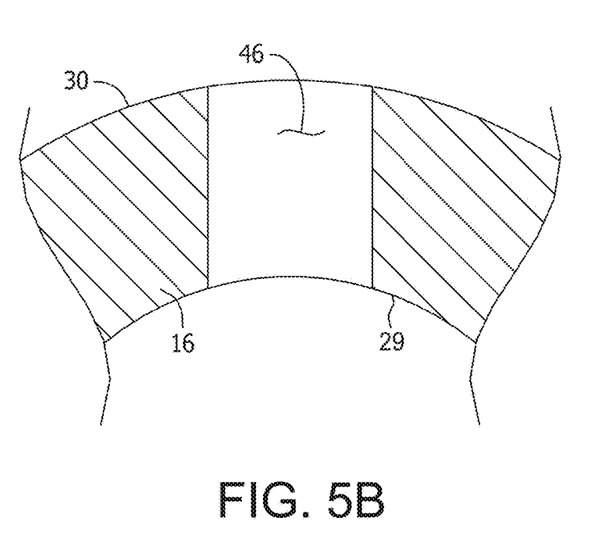

In some embodiments, the surface 30 of the anvil roll 16 may also comprise one or more vacuum holes 46, as seen in FIG. 5B, which do not comprise a generally uniform cross-section. That is, and unlike the vacuum holes 32, the vacuum holes 46 may have a varying diameter along its axial length. For example, in the embodiment depicted in FIG. 5B, the vacuum hole 46 comprises a chamfered top, with the diameter of the vacuum hole being greatest adjacent the outer surface 30 of the anvil roll 16 and becoming smaller along the axial length of the vacuum hole. As such, the walls of the chamfered vacuum hole 46 may form a greater angle with the surface 30 of the anvil roll 16 than the walls that the vacuum hole 32 forms with the surface of the anvil roll.

In some embodiments, one or more of the chamfered vacuum holes 46 may be provided in a region that ultimately abuts the fastening material 28 in order to reduce, e.g., the friction between the fastening material and the surface 30 of the anvil roll 16 when the incoming web 12 slips on the anvil roll. That is, because the walls of the chamfered vacuum hole 46 forms a greater angle with the outer surface 30 of the anvil roll 16 than the walls of the vacuum hole 32, the fastening material 28 will more readily slip along the abutting surfaces (i.e., the surface of the anvil roll and the side wall of the vacuum hole). In such embodiments, the fastening material 28 will be less likely to deform or shear off than if it would otherwise come in contact with the approximately right angle that the side walls of the vacuum hole 32 form with the surface 30 of the anvil roll 16.

For example, in embodiments where the fastening material 28 comprises a polymer hook material, the hooks may be prone to bending, deforming, or even shearing when they come into contact with the anvil roll 16 and, more particularly, when they come in contact with the side walls of the vacuum holes 32 of the anvil roll. However, the polymer hooks may deform, bend, or shear less or even not at all when they come in contact with the chamfered vacuum holes 46 of the anvil roll 16, because, as discussed, the polymer hooks can more readily slide along the abutting surfaces of the vacuum holes and the surface 30 of the anvil roll 16 due to the chamfer formed between the walls of the vacuum hole and the surface 30 of the anvil roll.

Figure 5C:
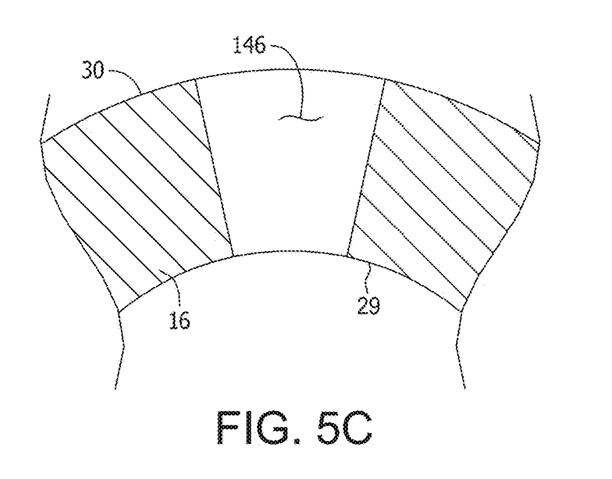
Figure 5D:
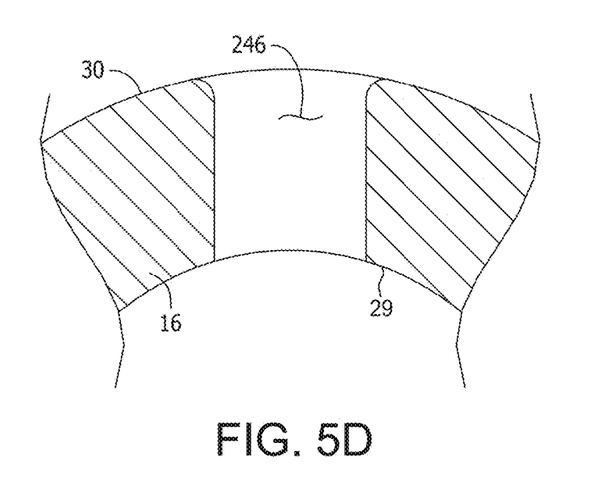

It is understood that the cross-sectional profile of a vacuum hole used in the reduced-vacuum region 36 is not limited to that depicted in FIG. 5B (i.e., a chamfered cross-section), but rather may be any suitable cross-section which reduces the friction force caused by the fastening material 28 slipping along the surface 30 of the anvil roll 16. For example, in other suitable embodiments, the cross-section of a vacuum hole 146 provided in the reduced-vacuum region 36 may be generally shaped as a frustum (as depicted in FIG. 5C), may be generally cylindrical but comprise rounded edges where the side walls of the vacuum hole 246 meet the surface 30 of the anvil roll 16 (as depicted in FIG. 5D), or may comprise any other suitable cross-section such that a hook or other material sliding along the surface of the anvil roll is not readily deformed. As illustrated in FIG. 5C, the frustum vacuum hole 146 tapers inward from the outer surface 30 of the anvil roll 16 towards the inner surface. That is, the diameter of the vacuum hole 146 decreases from the outer surface to the inner surface. It is understood, however, that the diameter of the vacuum hole can increase from the outer surface to the inner surface.

Further, it should be appreciated that any of the above discussed configurations for reducing the vacuum pressure and/or friction force in the area of reduced-vacuum region 36 may be combined without departing from the scope of this disclosure. For example, in some embodiments, the vacuum holes 32 may be provided in the reduced-vacuum region 36, however may be provided less densely than those provided in the vacuum region 34 (thus reducing the vacuum pressure in that region), may be smaller than those provided in the vacuum region (thus reducing vacuum pressure and/or reducing the engagement of the fastening material 28 with the inside of the vacuum hole), and/or may comprise a different cross-sectional profile than those provided in the vacuum region (thus reducing the friction force between the sliding fastener material and the surface 30 of the anvil roll 16).

Figure 6:
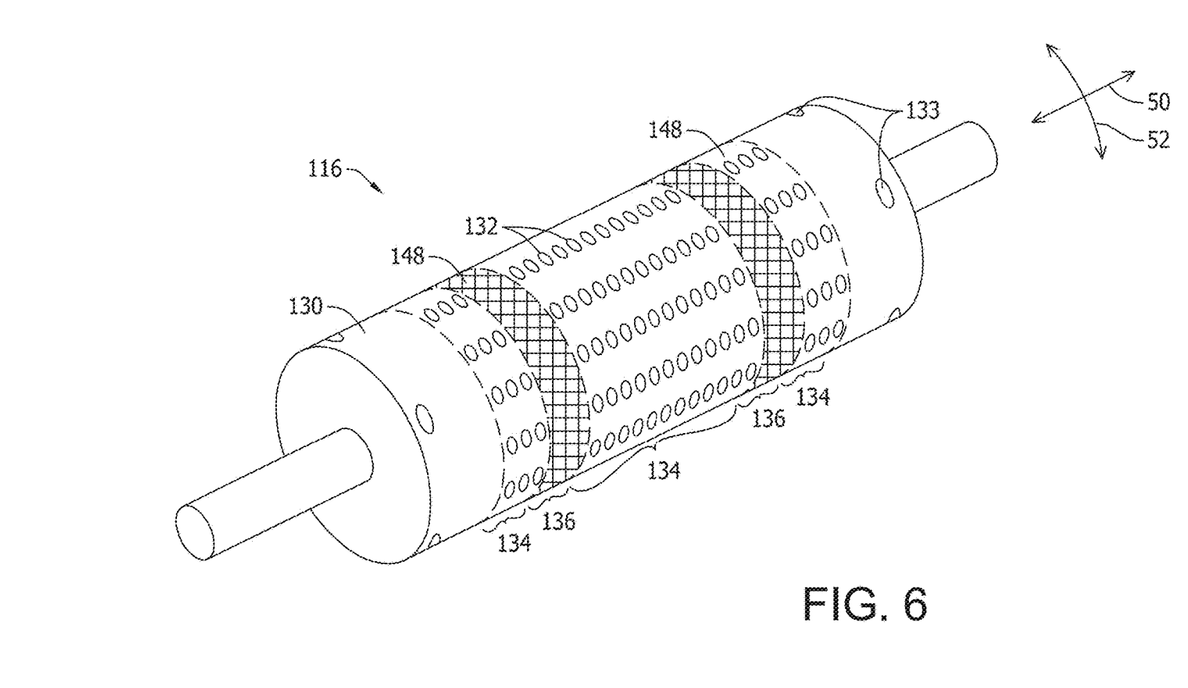
FIG. 6 is a perspective of another embodiment of an anvil roll used in the slip-and-cut system of FIG. 1.

Turning now to FIG. 6, in still other embodiments a material applied to and/or used to form an anvil roll and/or an anvil-roll plate in a region which ultimately abuts the fastening material 28 of the incoming web 12 may be different from a material applied to and/or forming the rest of the anvil roll and/or anvil-roll plate. For example, FIG. 6 depicts an anvil roll 116 comprising bands 148. As with the anvil roll 16 discussed in connection with FIGS. 3 and 4, the anvil roll 116 may be a vacuum drum with an anvil-roll plate attached to its circumference via one or more mounting holes 133. The bands 148 are provided on the anvil roll 16 at a location such that they will abut the fastening material 28 of the non-uniform incoming web 12 when the web is provided to and slips along the surface 130 of the anvil roll. Further, the bands 148 may be constructed from a material with different mechanical properties than the remainder of the surface 130 of the anvil roll 116 such that when a vacuum is drawn through the surface of the anvil roll via a vacuum source, vacuum regions 134 and reduced-vacuum regions 136 are formed. In such embodiments, the reduced-vacuum regions 136 may have a reduced vacuum pressure and/or friction force when ultimately contacting the incoming web 12 such that the fastening material 28 of the incoming web does deforms less than if the reduced-vacuum regions were formed from the same material as the vacuum regions.

For example, in some embodiments, the bands 148 may be formed of a wear-resistant material and/or may provide reduced frictional resistance in the reduced-vacuum regions 136 when in contact with the incoming web 12. For example, a TEFLON® coating, which is available from DuPont, or any other suitable material may be applied to an anvil roll 116 and/or anvil-roll plate even if the roll or the plate comprises vacuum holes 132 in the reduced-vacuum region 136. Accordingly, in some embodiments a known anvil roll may be retrofitted to provide at least some of the benefits as described herein by applying a suitable coating to regions of the anvil roll which will ultimately abut, e.g., the strips of fastening material 28 provided on the non-uniform incoming web 12.

In other embodiments, the bands 148 may be constructed from, e.g., a porous metal (such as porous steel), a mesh material, or the like. In such embodiments, a vacuum may still be drawn through the bands 148 due to the pores/openings provided in the porous metal and/or mesh material. Thus, a material (e.g., incoming web 12) may still be drawn to the surface 130 of the anvil roll 116. However, because the pores/openings provided in the bands 148 may be smaller than the vacuum holes 32 provided in the vacuum region 134 of anvil roll 116, a reduced vacuum pressure and/or friction force may be provided in the bands 148 resulting in a reduced-vacuum region 136 and leading to similar benefits as discussed above. Further, because in some embodiments the pores/openings of the porous metal/mesh material may be smaller in diameter than, e.g., the diameter of hooks or the like provided on the fastening material 28, the hooks will not engage the pores/openings when the incoming web 12 slips against the surface 130 of the anvil roll 116. Thus, even if the hooks are made from a relatively soft material (such as, e.g., polyethylene) the hooks may not be prone to bending, shearing, deforming, etc., as they slip across the surface 130 of the anvil roll 116.

Figure 7:
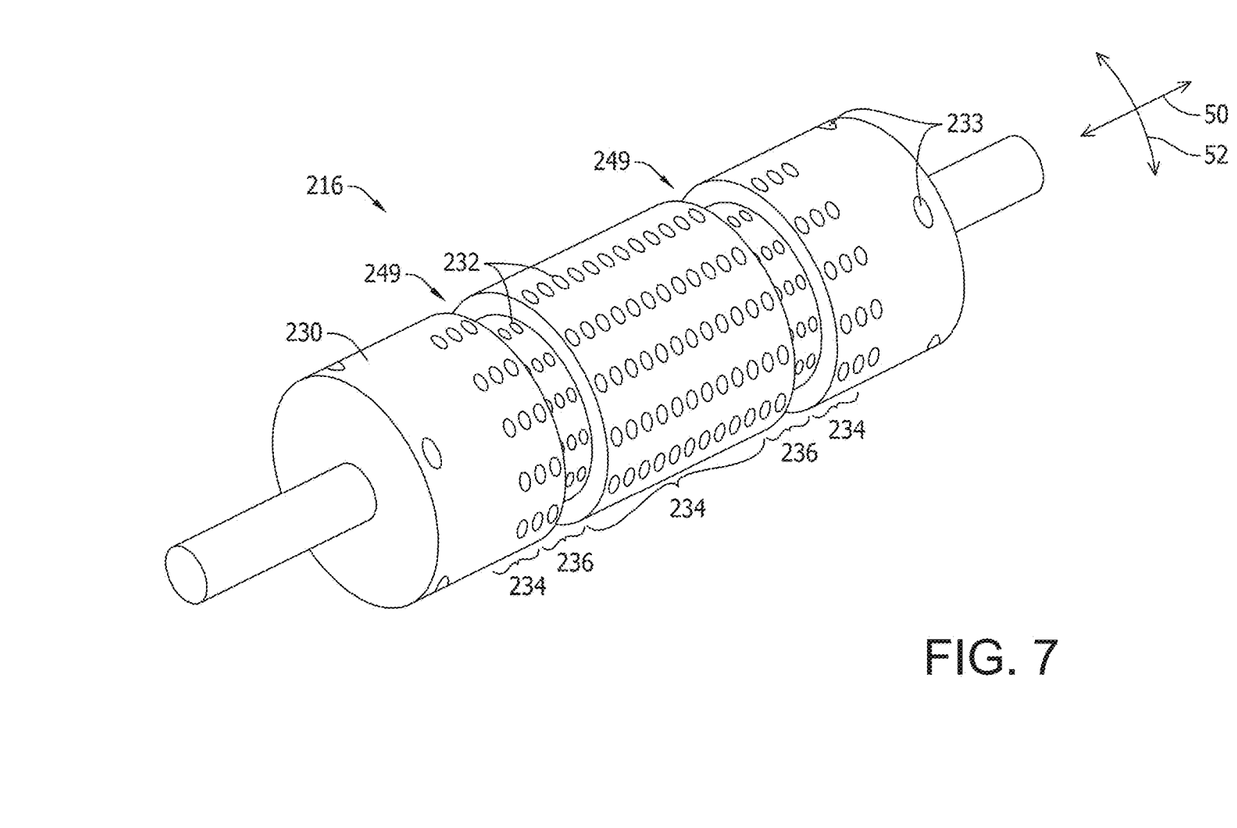
FIG. 7 is a perspective of yet another embodiment of an anvil roll used in the slip-and-cut system of FIG. 1.

Turning now to FIG. 7, in still other embodiments an anvil roll 216 used in the slip-and-cut system 10 of FIG. 1 may comprise one or more grooves 249 configured to receive the non-uniform incoming web 12. Specifically, the anvil roll 116 (or an anvil-roll plate configured to attach to a circumference of the vacuum roll via one or more mounting holes 233) may comprise the one or more grooves 249, each in a corresponding region on the surface 230 of the anvil roll 216 which ultimately abuts the fastening material 28 on the incoming web 12. Optionally (as depicted in FIG. 7), the surface 230 as well as the grooves 249 may comprise vacuum holes 232 which draw material to the surface of the anvil roll 216 by a vacuum source. It should be well understood given the benefit of this disclosure that in other embodiments the grooves 249 may not comprise any vacuum holes 232, may comprise fewer (i.e., less dense) and/or smaller vacuum holes than the vacuum regions 234 of the anvil roll 216, and/or may comprise vacuum holes having a different cross-sectional profile than the vacuum holes provided in the vacuum regions.

In this embodiment, the fastening material 28 (e.g., polymer hooks) may be less prone to bending, shearing, deforming, etc., when the incoming web 12 slips along the surface 230 of the anvil roll 216. That is, as the incoming web 12 is drawn to the surface 230 of the anvil roll 216 via a vacuum provided through the vacuum holes 232, the fastening material 28 will be received in the grooves 249. For example, a width and/or depth of the each groove 249 may be sufficiently sized in order to receive the fastening material 28 such that the fastening material does not contact the outer surface 230 of the anvil roll 216 when the incoming web 12 is provided to the slip-and-cut system 10. In another suitable embodiment, the depth of the groove 249 may be such that that the fastening material 28 only lightly contacts the outer surface 230 of the anvil roll 216 when the incoming web 12 is provided to the slip-and-cut system 10. For example, the depth of groove 249 may be slightly less than a thickness of the of the fastening material 28, and/or a vacuum applied to the anvil roll 216 may draw the fastening material into the groove such that the fastening material contacts the bottom surface of the groove, albeit with a less frictional force than if the anvil roll did not comprise the grooves 249.

In any event, while the base substrate 26 slips along the surface 230 of the anvil roll 216, the fastening material 28 may not slip along the surface 230 or, alternatively, may only lightly slip across the surface due to the depressions formed in the surface by the grooves 249. In such embodiments, the fastening material 28 (e.g., polymer hooks) will be less prone to bending, shearing, deforming, etc., because the hooks will not come into contact or, alternatively, only lightly contact the surface 230 of the anvil roll 216 during the slip-and-cut process.

In some embodiments, a vacuum pressure applied to the anvil roll 16 used in the slip-and-cut system 10 may vary in the lateral direction 50 of the anvil roll. For example, in some embodiments, an anvil roll 16 may comprise multiple vacuum chambers (not shown), with a different vacuum pressure applied to each chamber. In such embodiments, the vacuum chambers and corresponding negative pressures applied thereto may be configured such that a reduced vacuum pressure and/or friction force is applied to the incoming web 12 at regions of the surface 30 of the anvil roll 16 which ultimately abut the fastening material 28 of the incoming web (i.e., the reduced vacuum region 36).

For example, in some embodiments, the surface 30 of the anvil roll 16 may comprise vacuum holes 32 spaced regularly in the lateral direction 50 such that the vacuum holes are provided both in the vacuum region 34 and the reduced-vacuum region 36 (unlike the embodiment depicted in FIG. 3 where the vacuum holes are only provided in the vacuum region). However, the anvil roll 16 may further comprise multiple vacuum chambers with a different vacuum pressure applied to each chamber. Thus, the anvil roll 16 may comprise a plurality of vacuum chambers, with each chamber corresponding to and in fluid communication with one of the vacuum regions 34 or the reduced-vacuum regions 36. In one embodiment, the anvil roll may comprise two vacuum chambers, with a first of the two vacuum chambers in fluid communication with the vacuum regions 34, and the second of the two vacuum chambers in fluid communication with the reduced-vacuum regions 36.

In such embodiments, a first vacuum pressure may be applied to the vacuum chamber(s) in fluid communication with the vacuum regions 34, and a second vacuum pressure may be applied to the vacuum chamber(s) in fluid communication with the reduced-vacuum regions 36. Further, the vacuum pressure applied to the vacuum chamber(s) corresponding to the vacuum regions 34 may be a greater negative pressure (i.e., a greater vacuum) than the vacuum pressure applied to the vacuum chamber(s) corresponding to the reduced-vacuum regions 36. As such, material (e.g., the incoming web 12) slipping along the surface 30 of the anvil roll 16 in the reduced-vacuum regions 36 will experience a reduced vacuum pressure and/or friction force as compared to material slipping along the surface of the anvil roll in the vacuum regions 34. By way of an example, the chambers corresponding to the vacuum regions 34 may experience a vacuum in the range of approximately 1 to 20 inches of water, and the chambers corresponding to the reduced-vacuum regions 36 may experience a vacuum of significantly less (e.g., half or less) than the vacuum regions, such as, e.g., no vacuum, a vacuum in the range of 0.5 to 10 inches of water, etc. It is also contemplated that in other suitable embodiments, a positive pressure can be applied in the reduced-vacuum regions 36 to lessen the friction between the fastening material 28 and the outer surface of the anvil roll. Accordingly, a portion of a material (e.g., fastening material 28 of the incoming web 12) which ultimately abuts and slips against the reduced-vacuum regions 36 may be less prone to bending, shearing, deforming, etc., as discussed above.

The slip-and-cut system 10 and any of the above anvil rolls 16, 116, 216 and/or anvil plates 38 as described herein may be used to apply a discrete segment 22 to a product web 24 to form portions of an absorbent article such as a diaper or the like, particularly when the segment is formed from a web 12 having a non-uniform anvil-facing surface 25. For example, commonly owned U.S. patent application Ser. No. 13/953,364 entitled "Folded Absorbent Article with a Fastening System," Ser. No. 13/953,380 entitled "Absorbent Article Having a Fastening System," and Ser. No. 13/953,396 entitled "Absorbent Article Having a Fastening System With Low Stiffness," which were each filed on Jul. 29, 2013, and which are each incorporated herein by reference in its entirety, describe an absorbent article comprising a primary second fastening component and secondary first fastening component disposed on an outside cover of a diaper. Some embodiments of the slip-and-cut system 10 described herein may be used when manufacturing the diaper described in each referenced application in order to place the primary second fastening component and/or secondary first fastening component on the outside cover of the diaper.

For example, a web may be provided to the slip-and-cut system 10 which comprises a base substrate formed from the primary secondary fastening component material (e.g., a nonwoven loop material) and two strips extruded onto or otherwise attached to the base substrate formed from the secondary first fastening component material (e.g., a hook material such as a polymer hook material). In such embodiments, when the web comprising the primary second fastening component and the secondary first fastening component is provided to the slip-and-cut system 10, the secondary first fastening component may abut and slip against the reduced-vacuum region 36, 136, 236 of the anvil roll 16, 116, 216, thus reducing or eliminating bending, shearing, or deforming of the hooks which otherwise might occur if the anvil roll did not comprise the reduced-vacuum region.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A curved anvil-roll plate having a first end and a second end spaced longitudinally from the first end, the curved anvil-roll plate configured to contact a web comprising a first region having a first characteristic and a second region having a second characteristic different than the first characteristic, the curved anvil-roll plate comprising:
   a substantially arcuate wall comprising an inner surface and a cylindrical outer surface, free of grooves, defined between the first end and the second end of the curved anvil-roll plate;
   a plurality of vacuum holes extending between the inner and outer surfaces and configured to be in fluid communication with a vacuum source, the plurality of vacuum holes being in an arrangement that defines at least one vacuum region and at least one reduced-vacuum region, each of the at least one vacuum region and the at least one reduced-vacuum region extending circumferentially about the outer surface of the substantially arcuate wall, the at least one vacuum region being adapted to contact the first region of the web and the at least one reduced-vacuum region adapted to receive the second region of the web; and a band positioned within the at least one reduced-vacuum region and extending about a full circumference of the substantially arcuate wall, the band constructed of material of a first type and configured to have a reduced friction force relative to a remainder of the cylindrical outer surface, the remainder of the cylindrical outer surface constructed of material of a second type different from the first type, wherein the plurality of vacuum holes are configured such that, when attached to the vacuum source, a vacuum pressure at the at least one vacuum region is greater than a pressure at the at least one reduced-vacuum region so that the first region of the web is held against the plate with a greater force than the second region.

2. The curved anvil-roll plate of claim 1, wherein a number of vacuum holes per unit area in the reduced-vacuum region is less than a number of vacuum holes per unit area in the vacuum region.

3. The curved anvil-roll plate of claim 2, wherein the reduced-vacuum region is free of vacuum holes.

4. The curved anvil-roll plate of claim 1, wherein the band is constructed of at least one of a porous metal and a mesh material.

5. A curved anvil-roll plate having a first end and a second end spaced longitudinally from the first end, the curved anvil-roll plate configured to contact a web comprising at least one first region having a first characteristic and at least one second region having a second characteristic different than the first characteristic, the curved anvil-roll plate comprising:

a substantially arcuate wall comprising an inner surface and a cylindrical outer surface, free of grooves, defined between the first end and the second end of the curved anvil-roll plate; and a plurality of vacuum holes extending between the inner and outer surfaces and configured to be in fluid communication with a vacuum source, the plurality of vacuum holes in an arrangement that defines at least one vacuum region including a first vacuum region, a second vacuum region, and a third vacuum region, and at least one reduced-vacuum region including a first reduced-vacuum region and a second reduced-vacuum region, the first reduced-vacuum region positioned between the first and second vacuum regions, and the second reduced-vacuum region positioned between the second and third vacuum regions, the at least one vacuum region and the at least one reduced-vacuum region each extending circumferentially about the outer surface of the substantially arcuate wall, the at least one vacuum region adapted to contact the at least one first region of the web and the at least one reduced-vacuum region adapted to receive the at least one second region of the web, wherein the plurality of vacuum holes are configured such that, when attached to the vacuum source, a vacuum pressure at the at least one vacuum region is greater than a pressure at the at least one reduced-vacuum region so that the at least one first region of the web is held against the plate with a greater force than the at least one second region, wherein the plurality of vacuum holes comprises a first type of vacuum hole and a second type of vacuum hole different than the first type of vacuum hole, wherein the first type of vacuum hole is only provided in the at least one vacuum region, and wherein the second type of vacuum hole is only provided in the at least one reduced-vacuum region.

6. The curved anvil-roll plate of claim 5, wherein the second type of vacuum hole has a diameter which is smaller than a diameter of the first type of vacuum hole.

7. The curved anvil-roll plate of claim 5, wherein the second type of vacuum hole comprises a cross-sectional profile that is different than a cross-sectional profile of the first type of vacuum hole.

8. The curved anvil-roll plate of claim 7, wherein the second type of vacuum hole comprises one of a chamfered cross-sectional profile, a frustum cross-sectional profile, and a rounded edge cross-sectional profile.

9. The curved anvil-roll plate of claim 7, wherein each of the second type of vacuum hole has a varying diameter along its axial length.

10. The curved anvil-roll plate of claim 9, wherein each of the first type of vacuum hole has a uniform diameter along its axial length.

11. The curved anvil-roll plate of claim 7, wherein each of the second type of vacuum hole has a chamfered top edge.

12. The curved anvil-roll plate of claim 7, wherein each of the second type of vacuum hole is frustum.

13. The curved anvil-roll plate of claim 12, wherein each of the first type of vacuum hole is cylindrical.

14. The curved anvil-roll plate of claim 5, wherein each of the second type of vacuum hole is configured to reduce the friction force caused by the second region of the web slipping along the at least one reduced-vacuum region.

15. A curved anvil-roll plate having a first end and a second end spaced longitudinally from the first end, the curved anvil-roll plate configured to contact a web having at least one first region and at least one second region, the curved anvil-roll plate comprising:

a substantially arcuate wall comprising an inner surface and a cylindrical outer surface, free of grooves, defined between the first end and the second end of the curved anvil-roll plate, the arcuate wall defining a radius of curvature of the plate;

a first plurality of vacuum holes arranged in the substantially arcuate wall such that a first vacuum region is defined at the outer surface, the first vacuum region adapted to contact the at least one first region of the web, extending about a full circumference of the arcuate wall along the radius of curvature, and configured to be in fluid communication with a vacuum source;

a second plurality of vacuum holes arranged in the substantially arcuate wall such that a second vacuum region is defined at the outer surface, the second vacuum region adapted to contact the at least one first region of the web, extending about a full circumference of the arcuate wall along the radius of curvature, and configured to be in fluid communication with a vacuum source; and a third plurality of vacuum holes arranged in the substantially arcuate wall such that a third vacuum region is defined at the outer surface, the third vacuum region adapted to contact the at least one first region of the web, extending about a full circumference of the arcuate wall along the radius of curvature, and configured to be in fluid communication with a vacuum source, wherein the first, second, and third pluralities of vacuum holes are spaced from each other such that a first reduced-vacuum region is defined between the first and second pluralities of vacuum holes, and a second reduced-vacuum region is defined between the second and third pluralities of vacuum holes, the first and second reduced-vacuum regions adapted to receive the at least one second region of the web, first and second reduced-vacuum regions being free of holes and extending about a full circumference of the arcuate wall along the radius of curvature, wherein the first, second, and third pluralities of vacuum holes are the same type of vacuum hole, and are configured such that, when attached to the vacuum source, a vacuum pressure at the first, second, and third vacuum regions is greater than a pressure at the first and second reduced-vacuum regions so that the first region of the web is held against the plate with a greater force than the second region.

16. The curved anvil-roll plate of claim 15, wherein the first, second, and third vacuum regions are constructed of a first type of material and the at least one first and second reduced-vacuum regions are constructed of a second type of material that differs from the first type of material.

* * * * *